United States Patent [19]

Radlmann et al.

[11] 4,010,104

[45] Mar. 1, 1977

[54] SOLUTIONS OF NEW COMPLEX ANTIMONY COMPOUNDS

[75] Inventors: Eduard Radlmann; Heinz Schaffner; Günter Lorenz; Günther Nischk, all of Dormagen, Germany

[73] Assignee: Bayer Aktiengesellschaft, Leverkusen, Germany

[22] Filed: May 8, 1975

[21] Appl. No.: 575,698

[30] Foreign Application Priority Data

May 8, 1974 Germany ............... 2422141

[52] U.S. Cl. .................. 252/8.1; 260/446; 260/32.6 N

[51] Int. Cl.² ............ B27K 3/00; C09D 5/18; C07F 9/90

[58] Field of Search ......... 252/8.1; 260/446, 29.3 T

[56] References Cited

UNITED STATES PATENTS

| 3,245,958 | 4/1966 | Himlersinn | 260/446 |
| 3,411,115 | 3/1968 | Stamm | 260/446 |
| 3,654,179 | 4/1972 | Yates | 260/446 |
| 3,718,584 | 2/1973 | Beste et al. | 252/8.1 |
| 3,728,367 | 4/1973 | Yates | 260/446 |

FOREIGN PATENTS OR APPLICATIONS 2,159,174 8/1972 Germany ............ 260/446

*Primary Examiner*—Benjamin R. Padgett
*Assistant Examiner*—Josephine Lloyd
*Attorney, Agent, or Firm*—Plumley and Tyner

[57] ABSTRACT

The invention relates to solutions of complex antimony compounds substantially insoluble in water which are produced by reacting antimony oxides with α-hydroxy carboxylic acids and further reaction with monoisocyanates as well as a process for the production of these solutions.

The solutions according to the invention may be added to solutions of acrylonitrile polymers and copolymers and they improve the non-inflammability of shaped articles produced thereof.

14 Claims, No Drawings

SOLUTIONS OF NEW COMPLEX ANTIMONY COMPOUNDS

This invention relates to solutions in organic solvents of antimony compounds substantially insoluble in water, which solutions may be added to solutions of acrylonitrile and vinyl or vinylidene halide copolymers, are compatible with those solutions and, as synergists, distinctly improve the non-inflammability of shaped articles of mixtures of this kind.

It is known that antimony(III) and antimony(V) α-hydroxy carboxylic acid complexes can be prepared from the corresponding antimony halides in polar organic solvents by separating off the halogen by precipitating ammonium halide and adding an α-hydroxy carboxylic acid such as, for example, tartaric acid (U.S. Pat. No. 3,728,367 and DOS No. 2,159,174). In this way, complexes completely free from halogen or complexes still containing halogen are obtained, depending upon the quantity of ammonia used. Although complexes of this kind are miscible with solutions of copolymers of acrylonitrile and vinyl or vinylidene halides, they are attended by the serious disadvantage (in the case of the halogen-free compleses) of being soluble in water in all proportions and (in the case of the halogen-containing complexes) of undergoing partial hydrolysis when water is added, resulting in the formation of hydrogen halide which gives rise to corrosion in the apparatus used. In either case, the solubility of the complexes in water means that large quantities of the antimony are washed out and, hence, are ineffectual after the polymer solution has been processed to form shaped articles, for example filaments, by the conventional wet after-treatment procedures.

It is an object of this invention to provide solutions of complex antimony compounds which do not have the above-mentioned disadvantages.

It is a further object of this invention to provide a process for the production of these solutions.

Other objects will be evident from the following description and the Examples.

These objects are accomplished by a solution in a polar organic solvent of a complex reaction product of an antimony oxide with an α-hydroxy carboxylic acid which reaction product has been further reacted with a monoisocyanate and by a process for the production of a solution in a polar organic solvent of a complex antimony compound substantially insoluble in water, which comprises reacting an antimony oxide with an excess of an α-hydroxy carboxylic acid in a polar organic solvent at a temperature of from 100° to 200° C to form a clear solution and converting the excess carboxyl groups with a monoisocyanate at temperatures below 100° C into the corresponding amide groups.

The antimony oxides used are $Sb_2O_3$ and $Sb_2O_5$, preferably $Sb_2O_3$.

Examples of suitable α-hydroxy carboxylic acids include tartaric acid, malic acid, lactic acid, glycolic acid, citric acid, mucic acid and glyceric acid. Tartaric acid, malic acid and lactic acid are preferably used.

Suitable monoisocyanates are compounds corresponding to the general formula $R-N=C=O$, where R is a linear or branched alkyl radical with from 1 to 20 carbon atoms, or the radical:

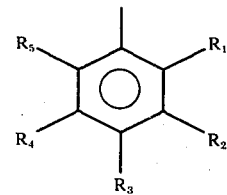

in which
$R_1$, $R_2$, $R_3$, $R_4$ and $R_5$, which may be identical or different, each represents hydrogen, an alkyl radical with from 1 to 5 carbon atoms of fluorine, chlorine or bromine.

Suitable polar organic solvents include formamide, monomethyl formamide, dimethyl formamide, acetamide, monomethyl acetamide, dimethyl acetamide, tetramethyl urea, N-methyl pyrrolidone and dimethyl sulphoxide. Dimethyl formamide and dimethyl acetamide are particularly preferred solvents.

The following procedure, for example, may be adopted for preparing the new compounds by the process according to the invention:

Antimony(III) or (V) oxide is heated under nitrogen at 100° to 200° C with an α-hydroxy carboxylic acid, for example tartaric acid, in a molar ratio of from 1:2 to 1:4 (ratio of Sb to α-hydroxy carboxylic acid) in the presence of from 30 to 100% by weight of a polar organic solvent, accompanied by the elimination of water, until a solution is formed. The solution is then cooled to temperatures below 100° C and diluted with more polar solvent (depending upon the application envisaged), and the stoichiometric quantity (based on the free carboxyl groups) of a monoisocyanate is added. Carbonamide groups are formed, their formation being accompanied by the evolution of carbon dioxide. The solutions obtained are colourless to pale yellow in colour and may be used as polymer additives as such, i.e. without any need for further purification. If the solvent is removed by distillation, a substantially colourless solid residue is left. The great advantage of this procedure is the fact that it is possible to to use antimony oxides, preferably antimony trioxide, as the starting antimony compound. There is no need to start with antimony halides and, hence, to remove the halogen by precipitation with ammonia. Accordingly, the invention provides non-hydrolysing, i.e. non-corrosive additives, which are insoluble in water and, hence, cannot be washed out during the usual aftertreatments.

Since, according to the invention, antimony and the α-hydroxy carboxylic acid are used in a molar ratio of from 1:2 to 1:4, reaction mixtures are generally formed. According to IR and NMR analyses, the major constituent, as will be demonstrated with reference by way of example to the reaction of malic acid, antimony trioxide and 3,4-dichlorophenyl isocyanate, is probably

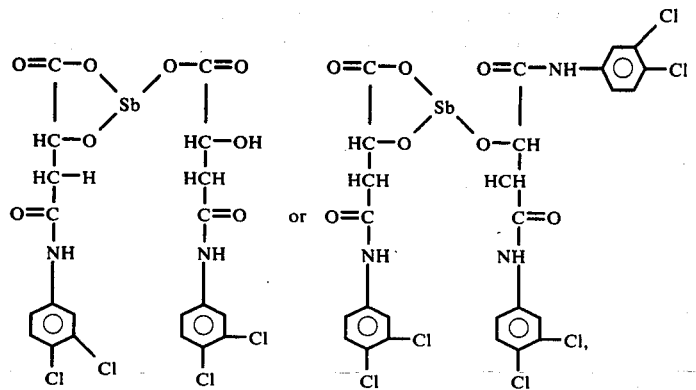

whereas structures such as, for example,

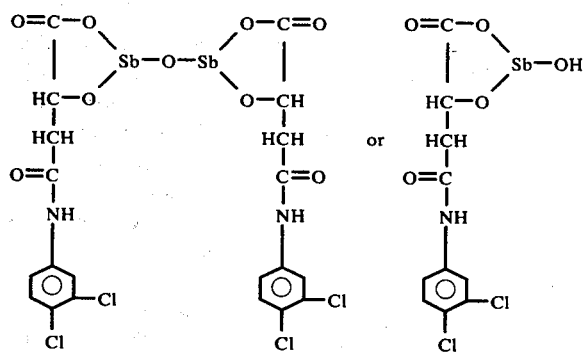

are present in smaller quantities. In cases where more than 2 mols of malic acid are used per mol of antimony, the reaction mixture also contains malic acid diamide of the formula:

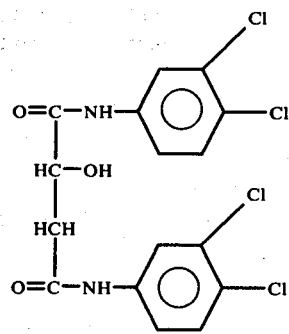

By virtue of their substantial insolubility in water, their high solubility in organic solvents and their compatibility with acrylonitrile/vinyl and vinylidene halide copolymers, the new reaction products according to the invention represent extremely effective corrosion-free flameproofing additives which cannot be washed out with water.

The following Examples are to further illustrate the invention without limiting it.

EXAMPLE 1 (Solution A)

150 parts by weight of tartaric acid are dissolved at approximately 100° C in 600 parts by weight of dimethyl formamide. Following the addition of 72.9 parts by weight of antimony trioxide, the temperature is increased with stirring to 150° C while nitrogen is passed over. Under these conditions, a clear solution is formed after about 55 minutes, during which water is distilled off. After cooling to 20° C, another 600 parts by weight of dimethyl formamide are added and phenyl isocyanate is added dropwise to the almost colourless solution at 20° to 40° C until there is no further evolution of carbon dioxide. 136.5 parts by weight have to be added to achieve this result. The reaction mixture is then stirred at 40° C for 2 hours, during which a slight deposit may form, although it is completely dissolved again on admixture with a copolymer of acrylonitrile and vinyl or vinylidene chloride. The molar ratio of tartaric acid to antimony is 2:1. Whereas antimony/tartaric acid complexes are soluble in water, the product precipitates when water is added to it.

EXAMPLE 2 (Solution B)

750 parts by weight of tartaric acid and 364 parts by weight of antimony trioxide, together with 400 parts by weight of dimethyl formamide, are heated with stirring to 150° C over a period of about 30 minutes, during which nitrogen is passed over and water is distilled off, until a clear solution is formed. The resulting solution is then dilated with another 1500 parts by weight of dimethyl formamide, cooled to 25° C and a solution of 290 parts by weight of methyl isocyanate in 500 parts by weight of dimethyl formamide is added dropwise in such a way that the temperature does not exceed 40° C. The evolution of $CO_2$ stops after a little more isocyanate is added. The reaction mixture is then stirred for 1.5 hours at 40° C. A small deposit may crystallise out of the colourless solution in the event of prolonged standing, although it disappears completely on admixture with an acrylonitrile-vinyl chloride copolymer solution in dimethyl formamide. The addition of water to the solution of the complex antimony compound causes the compound to precipitate.

EXAMPLE 3 (Solution C)

364.3 parts by weight of antimony trioxide and 400 parts by weight of dimethyl acetamide, together with 825 parts by weight of tartaric acid, are heated with stirring to 155° C over a period of 40 minutes, during which nitrogen is passed over and water is distilled off, until a clear melt is obtained. The melt is then diluted with another 2000 parts by weight of dimethyl acetamide, cooled to 20° C and 1128 parts by weight of 3,4-dichlorophenyl isocyanate are added in portions, so that the temperature does not exceed 40° C. The evolution of $CO_2$ stops after the above-mentioned quantity of isocyanate has been added. The almost colourless solution is then stirred for 3 hours at 40° C. Any deposit which may form dissolves completely on admixture with an acrylonitrile/vinylidene chloride copolymer solution in dimethyl acetamide.

EXAMPLE 4 (Solution D)

670 parts by weight of malic acid, 364.3 parts by weight of antimony trioxide and 500 parts by weight of dimethyl formamide are heated with stirring to 150° C. Water distils off until a clear solution is formed. The solution is then diluted with 1800 parts by weight of dimethyl formamide, cooled to 20° C and n-butyl isocyanate is added in portions at 20° to 40° C until the evolution of $CO_2$ stops. 499 parts by weight of isocyanate are consumed. The solution formed is only the palest yellow in colour and is stirred for 2 hours at 40° C. Any deposit which may form is completely redissolved when the solution is added to a copolymer solution in dimethyl formamide. The complex antimony compound is insoluble in water.

EXAMPLE 5

The complex antimony solutions A, B, C and D described in Examples 1 to 4 are added in various quantities to a 35% dimethyl formamide solution of an acrylonitrile/vinylidene chloride copolymer (composition: 58.6% of acrylonitrile, 38.5% of vinylidene chloride and 2.9% of sodium methallyl sulphonate) with a K-value (according to Fikentscher) of 74. The polymer solutions with the additions are then dry spun into filaments by known methods. The filaments thus produced are stretched in hot water and washed in the usual way.

The results of burning tests (vertical burning test as specified in DIN 53906) carried out on pieces of fibre-yarn knitting are set out in the following Table:

| Solution Added | Antimony Content [%] added | Found in piece of knitting | Vertical burning test According to DIN 53866 | | |
|---|---|---|---|---|---|
| | | | Ignition time secs. | Burning time * secs | Length burnt [cm] max 35 cm |
| — Comparison test without any addition | 0 | 0 | 3 | 48 | 32.5 |
| | | | 3 | 29 | 32.5 |
| | | | 3 | 27 | 20.0 |
| | | | 15 | 25 | 32.5 |
| | | | 15 | 27 | 32.5 |
| | | | 15 | 26 | 32.5 |
| A | 0.5 | 0.4 | 3 | 12 | 11.0 |
| | | | 3 | 15 | 11.5 |
| | | | 3 | 17 | 9.0 |
| | | | 15 | 22 | 12.0 |
| | | | 15 | 15 | 14.5 |
| | | | 15 | 18 | 15.5 |
| A | 1.0 | 0.9 | 3 | — | 4.5 |
| | | | 3 | — | 5.0 |
| | | | 3 | 2 | 4.0 |
| | | | 15 | — | 10.0 |
| | | | 15 | 2 | 11.5 |
| | | | 15 | 5 | 13.0 |
| A | 1.5 | 1.5 | 3 | — | 2.0 |
| | | | 3 | — | 1.0 |
| | | | 3 | — | 1.5 |
| | | | 15 | — | 3.5 |
| | | | 15 | 1 | 3.0 |
| | | | 15 | — | 3.0 |
| B | 1.5 | 1.4 | 3 | 1 | 1.0 |
| | | | 3 | — | 2.0 |
| | | | 3 | — | 1.0 |
| | | | 15 | 1 | 3.0 |
| | | | 15 | — | 3.5 |
| | | | 15 | — | 3.0 |
| C | 1.8 | 1.6 | 3 | — | 1.0 |
| | | | 3 | — | 1.0 |
| | | | 3 | — | 1.5 |
| | | | 15 | — | 1.0 |
| | | | 15 | — | 1.5 |
| | | | 15 | — | 2.0 |
| D | 1.5 | 1.5 | 3 | 1 | 2.0 |
| | | | 3 | 2 | 1.0 |
| | | | 3 | — | 1.0 |
| | | | 15 | — | 3.0 |
| | | | 15 | — | 3.0 |
| | | | 15 | 1 | 3.0 |

*Following removal of the ignition flame.

We claim:
1. A fire retardant solution in a polar organic solvent of a complex reaction product of an antimony oxide with an α-hydroxy carboxylic acid which reaction product has been further reacted with a monoisocyanate.

2. The solution of claim 1, wherein said polar organic solvent is a member selected from the group consisting of dimethyl formamide, dimethyl acetamide, N-methyl pyrrolidone and dimethyl sulphoxide.

3. The solution of claim 1, wherein said antimony oxide is antimony trioxide.

4. The solution of claim 1, wherein said α-hydroxy carboxylic acid is a member selected from the group consisting of tartaric acid, malic acid and lactic acid.

5. The solution of claim 1, wherein said monoisocyanate is the compound corresponding to the general formula R—N=C=O, wherein R represents a linear or branched alkyl radical with from 1 to 20 carbon atoms, or the radical:

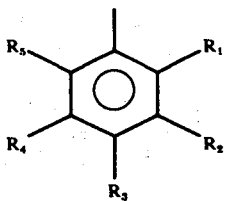

in which $R_1$, $R_2$, $R_3$, $R_4$ and $R_5$, which may be identical or different, each represents a member selected from the group consisting of hydrogen, an alkyl radical with from 1 to 5 carbon atoms, fluorine, chlorine and bromine.

6. A process for the production of a solution in a polar organic solvent of a complex antimony compound substantially insoluble in water, which comprises reacting an antimony oxide with an excess of an α-hydroxy carboxylic acid in a polar organic solvent at a temperature of from 100° to 200 C to form a clear solution and converting the excess carboxyl groups with a monoisocyanate at temperatures below 100° C into the corresponding amide groups.

7. The process of claim 6, wherein said polar organic solvent is a member selected from the group consisting of dimethyl formamide, dimethyl acetamide, N-methyl pyrrolidone and dimethyl sulphoxide.

8. The process of claim 6, wherein said antimony oxide is antimony trioxide.

9. The process of claim 6, wherein said α-hydroxy carboxylic acid is a member selected from the group consisting of tartaric acid, malic acid and lactic acid.

10. The process of claim 6, wherein said monoisocyanate is a compound corresponding to the general formula R—N=C=O, wherein R is a linear or branched alkyl radical with from 1 to 20 carbon atoms, or the radical:

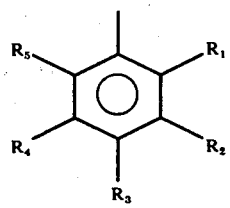

in which $R_1$, $R_2$, $R_3$, $R_4$ and $R_5$, which may be identical or different, each represents a member selected from the group consisting of hydrogen, an alkyl radical with from 1 to 5 carbon atoms, fluorine, chlorine and bromine.

11. The process of claim 6, wherein said reaction of said antimony oxide with said α-hydroxy carboxylic acid is carried out at a temperature of from 100° to 180° C.

12. The process of claim 6, wherein said reaction of said carboxyl groups with said monoisocyanate is carried out at a temperature of from 40° to 80° C.

13. The process of claim 6, wherein said molar excess of said α-hydroxy carboxylic acid to antimony is in the range of from 2:1 to 4:1.

14. The use of a solution of claim 1 as a flame retardant additive to a spinning solution of an acrylonitrile polymer or copolymers.

* * * * *